of Patent: Jun. 24, 1986

United States Patent [19]

Pitha

[11] Patent Number: 4,596,795
[45] Date of Patent: Jun. 24, 1986

[54] ADMINISTRATION OF SEX HORMONES IN THE FORM OF HYDROPHILIC CYCLODEXTRIN DERIVATIVES

[75] Inventor: Josef Pitha, Baltimore, Md.

[73] Assignee: The United States of America as represented by the Secretary, Dept. of Health & Human Services, Washington, D.C.

[21] Appl. No.: 603,839

[22] Filed: Apr. 25, 1984

[51] Int. Cl.$^4$ .............................................. A61K 31/70
[52] U.S. Cl. ...................................................... 514/58
[58] Field of Search ............... 424/238, 242, 243, 180; 514/58; 536/103

[56] References Cited

U.S. PATENT DOCUMENTS

| | | |
|---|---|---|
| 2,827,452 | 3/1958 | Schlenk et al. |
| 3,420,788 | 1/1969 | Solms . |
| 3,453,259 | 7/1969 | Parmerter et al. |
| 3,459,731 | 8/1969 | Gramen et al. |
| 4,383,992 | 5/1983 | Lipari ................................. 424/238 |

FOREIGN PATENT DOCUMENTS

| | | |
|---|---|---|
| 1244990 | 9/1971 | United Kingdom . |
| 1450960 | 9/1976 | United Kingdom . |

OTHER PUBLICATIONS

Fenyvesi et al. Water-Soluble Cyclodextrin Polymersing I. Int. Sympsoium on Cyclodextrins, p. 345 (Budapest, 1981).

Maeno, Liquid Crystal Element and Its Use, Chem. Abstracts 87 : 144000u (1977).

Kyowa Hakko Kogyo Co., Inclusion Compound of Medroxyprogesterone . . . and B–Cyclodextrin, Chem. Abstracts 98 : 8163z (1982).

Uekama et al., Inclusion Complexation of Steroid Hormones with Cyclodextrins . . ., Chem. Abstracts 96 : 149046j (1982).

*Primary Examiner*—Ethel G. Love
*Attorney, Agent, or Firm*—John S. Roberts, Jr.

[57] ABSTRACT

The administration of sex hormones, particularly testosteorne, progesterone and estradiol in the form of their complexes or inclusions with specific derivatives of cyclodextrins by the sublingual or buccal route results in effective transfer of these hormones into the systemic circulation, followed by only gradual elimination. To be effective in the above mode of administration, the derivatives of cyclodextrins must carry one or several substituents, each containing one or several hydroxy groups. Specially preferred are the following complexes: hydroxypropylbeta-cyclodextrin and poly-beta-cyclodextrin.

3 Claims, 5 Drawing Figures

ADMINISTRATION OF SEX HORMONES IN THE FORM OF HYDROPHILIC CYCLODEXTRIN DERIVATIVES

The present invention lies in certain hydrophilic cyclodextrin derivatives which enable effective oral administration of sex hormones, particularly testosterone, progesterone, and estradiol.

Condensation products of beta-cyclodextrin with propylene oxide or epichlorohydrin from water-soluble complexes with testosterone and other substances, such as progesterone and estradiol. Sublingual administration of tablets of these complexes leads to effective absorption and entry of these hormones into the systemic circulation, followed by only gradual elimination. Other cyclodextrin derivatives, a non-ionic detergent, or other modes of administration were ineffective by comparison.

Therapeutic use of sex hormones is required in the treatment of a number of diseases, including lack of natural hormones. However, effective treatment is difficult since these steroids are absorbed only slowly from the gastrointestinal tract and are rapidly cleared from circulating blood by the liver. Numerous attempts have been made to circumvent these problems, including the administration of huge doses of natural hormones, preparation of lipophilic pro-drugs of natural hormones which are injected intramuscularly and synthesis of analogs of natural hormones. The last approach resulted in preparations which are active but side effects were often significant.

The rationale of the present approach is to rely on physiological doses of natural hormones and to chemically modify additives of the pharmaceutical preparation in order to improve absorption of the hormone. The establishment of efficient and fast absorption would enable the use of a sublingual or rectal route of entry by which steroids would be protected from immediate metabolism by the liver.

From a practical point of view, various carbohydrates and chemically derivatized carbohydrates were used to solubilize or to disperse steroids in order to obtain a suitable drug form. In Example 1, post, there are a number of carbohydrates tested for solubility purposes. It was established that only solutions of testosterone in those cyclodextrin derivatives which are highly water soluble were effective. Furthermore, it was necessary that these preparations be kept in the mouth for several minutes (i.e., were administered sublingually). All other preparations lacked any activity.

The finding that a combination of testosterone, progesterone, or estradiol with hydroxypropyl-beta-cyclodextrin or with poly-beta-cyclodextrin is active only when absorbed from the oral cavity and not from the gastrointestinal tract is in accordance with the fast metabolism of sex hormones by the liver. The half-lives of these hormones in circulation are estimated to be only several minutes. The sublingual route is known to be less immediately affected by liver metabolism than entry from the gastrointestinal tract. Furthermore, possible metabolism of the drug by intestinal tissue, a phenomenon only recently appreciated, is avoided.

It was of interest to estimate the rates of elimination of testosterone administered by the sublingual route. The results are summarized in FIG. 1; testosterone's half-life in serum is about seventy minutes. The same figure also indicates that the same methods enable effective oral administration of progesterone and 17-beta-estradiol. In the therapeutic experiments which involved progesterone and 17-beta-estradiol, it was found that progesterone thus administered was eliminated from serum at a rate similar to that of testosterone, whereas elimination of estrogens was much slower. The experiments in Example 1 were performed on an adult male A, described in Example 2.

The effectiveness described entry of sex hormones into the systemic circulation of man due to the combination of high dissolution power of hydrophilic derivatives of cyclodextrins, the non-aggregated structure of their complexes with steroids, and to their low toxicity and irritancy of mouth tissue. To establish that this effectiveness is achieved by other similar compounds, we synthesized and evaluated the following additional preparations: (1) poly-alpha-cyclodextrin, (2) poly-gamma-cyclodextrin, (3) hydroxypropyl-alpha-cyclodextrin, (4) hydroxypropyl-gamma-cyclodextrin, and (5) trihydroxy-dioxadodecanyl-beta-cyclodextrin. These compounds were prepared in the same manner as the compounds detailed above the proper cyclodextrin and epichlorohydrin (compound 1 and 2 above) or propylene oxide (compounds 3 and 4 above) or 1,4-butanediol diglycidyl ether (compound 5 above). All of these compounds were tested for solubilization of testosterone, progesterone, and estradiol. These results are summarized in FIGS. 2, 3, and 4. These results indicate that all additional beta-cyclodextrin derivatives and all gamma-cyclodextrin derivatives are effective additives. Various glycosylated cyclodextrins, which can be obtained by either enzymatic or chemical methods and are as hydrophilic as above compounds, can also be expected to give positive results. On the other hand, none of the alpha-cyclodextrin derivatives studied achieved solubilization comparable to those obtained with the above compounds. Also, a sample of polyvinylpyrrolidone (average molecular weight 40,000) was used as a solubilizer in the above experiments, and proved to be ineffective.

Toxicity: The lack of untoward effects of poly-beta-cyclodextrin and of hydroxypropyl-beta-cyclodextrin was established by a study of laboratory mice (C57BL/6J strain, males; labelled "B") and on mice (white NIH random breed; labelled "W").

Intraperitoneal route: Compounds were applied in isotonic saline and animals were followed for at least a week after injection.

Poly-beta-cyclodextrin: (1) One B mouse, 15.35 g/kg; one B mouse, 10.7 g/kg; one mouse died after one day; (2) four W mice, 10 g/kg; all mice alive.

P.O. toxicity protocol: Three groups of B mice were used. One group ("Control") was used as a control, the second group ("Poly-BCD") was given (as the only source of liquid) a solution of poly-beta-cyclodextrin (1%) in water, and the third group ("HPBCD") was given (as the only source of liquid) a solution of hydroxypropyl-beta-cyclodextrin (1%) in water. The experiment was conducted for sixteen weeks; there were no deaths. Each week the weight change of the groups of mice was recorded. After sixteen weeks the mice were killed and the tissues were examined by a pathologist; serum was also collected and its cholesterol content was measured.

Weight changes of mice during the experiment are summarized in FIG. 5. Upon termination of the experiment, all mice were found substantially free of pathological changes except one of the controls. The data on this mouse were not included in the results given in Table 2. The livers of mice of the hydroxypropyl-beta-cyclodextrin group had slightly higher average weights than those of the other groups; nevertheless, no pathology was detected there. The cholesterol concentration in plasma did not differ significantly; i.e., average values of the three groups differed between themselves less than the standard deviations.

Material Information Disclosure

German Pat. No. 895,769 (1953)—complexes of drugs with cyclodextrins.

U.S. Pat. No. 2,827,452 Schlenk et al.—formation of complexes with alpha, beta, and gamma cyclodextrins.

Japanese Pat. No. 82130914 (Aug. 13, 1982)—describes the use of cyclodextrin crosslinked with epichlorohydrin to complex penicillin G.

U.S. Pat. No. 3,453,259 Parmerter et al.—describes ethers of cyclodextrins with 2,3-epoxy alcohols or halohydrins which may be used as "complexing agents in order to form inclusion compounds and complexes with various chemicals and materials in ways which are similar to those which are known relative to cyclodextrins."

U.S. Pat. No. 3,459,731 Gramen et al.—claims ethers of cyclodextrins with ethylene oxide and propylene oxide which may be used as various inclusion compounds.

U.S. Pat. No. 3,420,788 Solms—describes cyclodextrins crosslinked with epichlorohydrin and other bifunctional reagents.

British Pat. No. 1,244,990 (Sept. 2, 1977)—describes derivatives of cyclodextrin with poly-functional reactants, such as epichlorohydrin, formaldehyde, diepoxybutane, phosphorus oxychloride. These derivatives can be used in the separation of mixtures of substances or to protect unstable substances against oxidation, decomposition, etc.

DESCRIPTION OF THE FIGURES

FIG. 2.

DETAILED DESCRIPTION OF THE INVENTION

Figure 1:
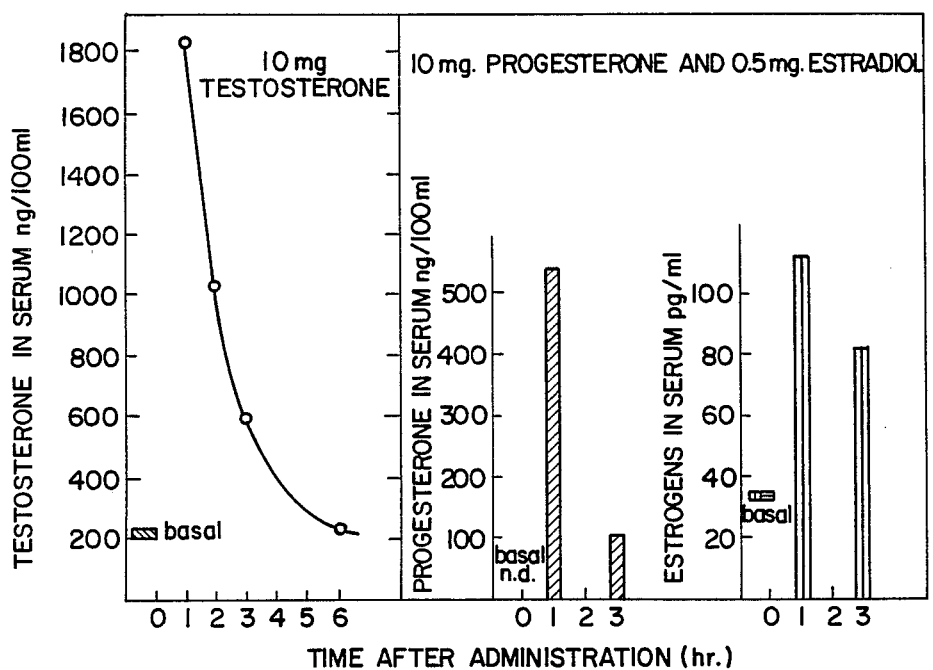
FIG. 1. Serum level of sex steroid hormones after sublingual administration of tablets containing (on left): testosterone (10 mg) in the form of its hydroxypropyl-beta-cyclodextrin complex; (on right): progesterone (10 mg) and estradiol (0.5 mg) in the same complexed form; tested on subject described in Table 1.
Figure 2:
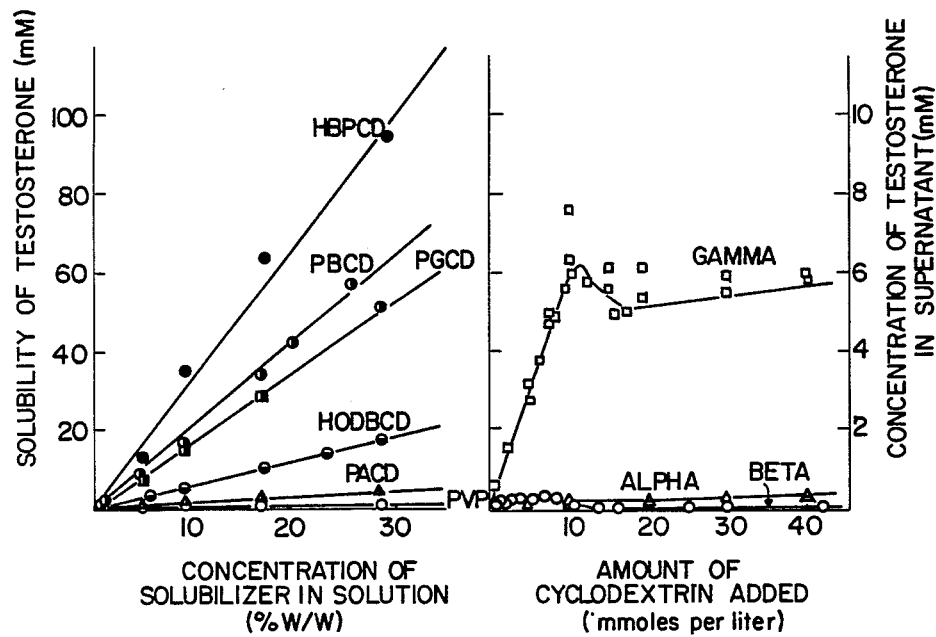
FIG. 2. Solubilization of testosterone by poly-vinyl-pyrrolidone (PVP), poly-alpha-cyclodextrin (PACD), by trihydroxydioxadodecanyl-beta-cyclodextrin (HODBCD), by poly-gamma-cyclodextrin (PGCD), poly-beta-cyclodextrin (PBCD), and by hydroxypropyl-beta-cyclodextrin (HPBCD). On right is shown limited solubilization of testosterone (note one order difference in the y-axis scale) by alpha, beta, and gamma-cyclodextrins.
Figure 3:
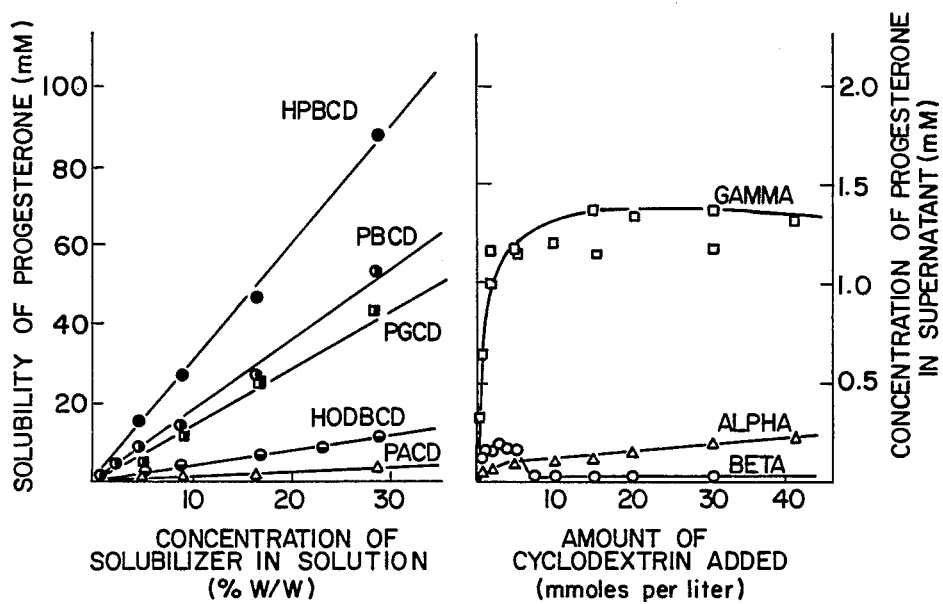
FIG. 3. Solubilization of progesterone by cyclodextrins and their derivatives. For abbreviations cmp.
Figure 4:
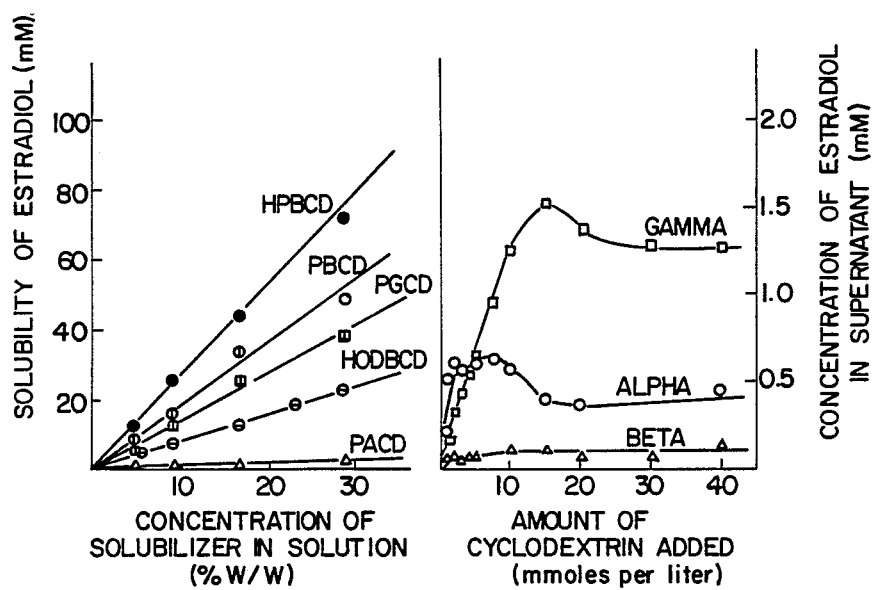
FIG. 4. Solubilization of estradiol by cyclodextrins and their derivatives. Abbreviations are the same as in FIG. 2.
Figure 5:
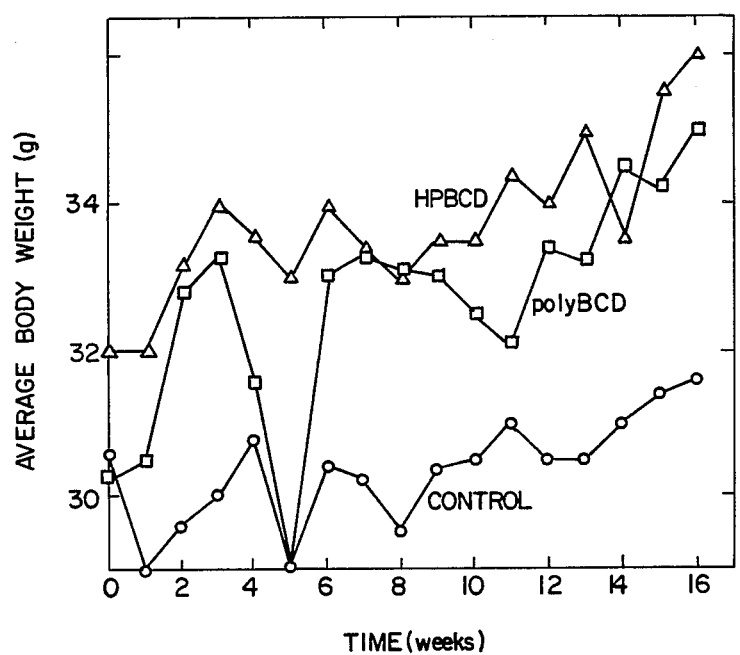
FIG. 5. Weight changes of treated and control groups of mice. Control n=5, poly-beta-cyclodextrin n=6, hydroxypropyl-cyclodextrin n=5.

Therapeutic use of sex hormones is required in the management of a number of diseases, including lack of natural hormones, many of them prominent in aging. The administration of sex hormones may be used also in manipulating the menstrual cycle resulting in birth control and premenstrual tension syndrome. These steroids are absorbed slowly from the gastrointestinal tract and are rapidly cleared from circulating blood by the liver. A mode of therapy relies on hydrolyzable derivatives of hormones which are dissolved in an oil and injected intramuscularly; alternatively, these derivatives may be transformed into a form suitable for implantation.

This invention discloses that rapid and complete dissolution of sex hormone preparations in the mouth, as achieved by hydrophilic cyclodextrin derivatives, enables an effective entry of these hormones into systemic circulation of a man and that elimination of these hormones from the circulation is only gradual. Only a specific type of dissolution of hormones is effective for this entry; dissolution aided by cyclodextrins themselves, hydrophobic cyclodextrin derivatives, or detergents did not enable effective entry.

In an inclusion complex of a sex hormone with one member of the group consisting of hydroxypropyl-beta-cyclodextrin and poly-beta-cyclodextrin a daily dosage is administered in the amount of 0.1–25 mg (buccal).

The following examples illustrate the claimed invention:

EXAMPLE 1

A number of carbohydrates, their chemical derivatives, and detergents were used to solubilize or to disperse testosterone, and the resulting drug forms were tested on a male with hypopituitary conditions. Results on effective additives and several related ones are given in Table 1, below.

Three of the additives were derivatives of beta-cyclodextrin. Beta-cyclodextrin is a product of enzymatic degradation of starch and contains seven glucose units joined in a circle by alpha 1→4 glycosidic bonds. Heptakis-2,6-di-O-methyl-beta-cyclodextrin (Table 1) is a derivative of beta-cyclodextrin, is more soluble in water and is a better solubilizer than the parent compound (Pitha, Life Sci., 29:307–311, 1981). Hydroxypropyl-beta-cyclodextrin and poly-beta-cyclodextrin are formed by condensation of beta-cyclodextrin with propylene oxide or with epichlorohydrin, respectively. The former contains one cyclodextrin moiety per molecule and has on the average of about one hydroxypropyl group per glucose unit (estimated from integral values of characteristic peaks in NMR spectra). Poly-beta-cyclodextrin is an oligomeric species; for the present invention a soluble preparation with an average molecular weight of 5600 was used. Both hydroxypropyl-beta-cyclodextrin and poly-beta-cyclodextrin are highly soluble in water (e.g., 40% solutions W/W are easily obtainable) and thus greatly differ from beta-cyclodextrin itself (saturated solution contains about 2% W/W). These compounds and their complexes with drugs, when obtained by freeze-drying of the solutions, are white, non-hydroscopic powders suitable for direct tableting. Tween 80, which was also evaluated in the present experiments (see Table 1), is a commercial non-ionic detergent (monooleate of polyoxyethylenesorbitan) which efficiently solubilizes steroids into water and is relatively non-toxic.

TABLE 1

Effects of Solubilizers on Testosterone Bioavailability*

| Treatment | Testosterone in Serum (ng/100 ml)** | |
|---|---|---|
| | Basal | At 2 hr after treatment |
| Testosterone (10 mg) in form of its heptakis-2,6-di-O-methyl-beta-cyclodextrin complex; dry powder administered sublingually | 330 | 330 |
| Testosterone (10 mg) solubilized by Tween 80 (25% W/W in water); the solution was administered sublingually | 370 | 430 |
| Testosterone (14 mg) in form of its poly-beta-cyclodextrin complex; the solution was administered sublingually | 240 | 1270 |
| Testosterone (10 mg) in form of its hydroxypropyl-beta-cyclodextrin complex; tablet was administered sublingually | 210 | 1020 |
| Testosterone (10 mg) in form of its hydroxypropyl-beta-cyclodextrin complex; dry material in hard gelatin capsule was swallowed | 530 | 480 |

*Subject defined in Example 2
**Assays performed by Bioscience Laboratories, Inc., Columbia, MD.

The effective absorption of sex hormones is a highly selective phenomenon (Table 1). Complexes of testosterone with beta-cyclodextrin were found relatively ineffective (results not shown). Heptakis-2,6-0-dimethyl-beta-cyclodextrin also had only marginal effects on the absorption of sex steroids from the oral cavity (Table 1). Additionally, this compound has slight toxicity. Dissolution of steroids by detergent (Tween 80) was ineffective as a means of improving the absorption of these hormones (Table 1).

Hydroxypropyl-beta-cyclodextrin and poly-beta-cyclodextrin effectively supported absorption of steroids from the oral cavity. The effectiveness achieved in this manner was impressive compared to other methods. Oral administration of 20 times higher doses of testosterone in conventional tablets led only to peak values of 300-900 ng/100 ml of testosterone in serum. Addition of polyethylene glycol derivatives only moderately improved this situation. The effective agents differ from the others in Table 1 in two points which contribute to the differences in effectiveness. While the ability of hydroxypropyl-beta-cyclodextrin and poly-beta-cyclodextrin to form complexes with drugs is about the same as other beta-cyclodextrins, these agents themselves and their complexes are much more soluble in water. Furthermore, compared to detergents the effective cyclodextrin derivatives do not form mycelles in which a steroid would dissolve; a single modecule of steroid is inserted into the beta-cyclodextrin cavity, and thus retains the potential for fast and mechanistically simple release of hormones. These features indicate that effective absorption of drugs from the oral cavity is primarily dependent on a speedy and effective dissolution of a drug in the saliva and then on barrier-free transfer from the solution to the oral tissue.

EXAMPLE 2

Subject J.P.: Caucasian male, 50 years old with hypopituitary condition which occurred and was diagnosed at the age of 47. Supplement of 200 μg of L-thyroxine, which J.P. receives daily, results in serum levels of 6 mcg/100 ml (cmp normal 5-12 mcg/100 ml) in intervals between testosterone supplementation the level of testosterone in serum was about 200 ng/100 ml (cmp normal 260-1120 ng/100 ml).

The effectiveness of this treatment is shown in Table 1.

TABLE 2

Average Weight (g) ± Standard Deviation (% of body weight)

| organ | Treatment | | |
|---|---|---|---|
| | control | poly-BCD | HPBCD |
| lungs | 0.20 ± 0.02 (0.63) | 0.18 ± 0.02 (0.51) | 0.18 ± 0.03 (0.50) |
| liver | 1.55 ± 0.16 (4.90) | 1.84 ± 0.19 (5.30) | 2.04 ± 0.04 (5.70) |
| heart | 0.17 ± 0.02 (0.54) | 0.18 ± 0.02 (0.51) | 0.20 ± 0.02 (0.55) |
| kidneys | 0.47 ± 0.05 (1.50) | 0.53 ± 0.06 (1.50) | 0.51 ± 0.04 (1.40) |
| spleen | 0.10 ± 0.01 (0.32) | 0.11 ± 0.03 (0.31) | 0.10 ± 0.01 (0.28) |
| # of aminals | 4 | 6 | 5 |

I claim:

1. A method of treating a human by sex hormone addition which comprises injecting by the buccal route a regimen of 0.1-25 mg per diem of a compound consisting of testosterone, progesterone, and estradiol as an inclusion complex with poly-β-cyclodextrin or hydroxypropyl-β-cyclodextrin.

2. The method of claim 1 wherein poly-β-cyclodextrin is utilized.

3. The method of claim 1 wherein hydroxypropyl-β-cyclodextrin is utilized.

* * * * *

UNITED STATES PATENT AND TRADEMARK OFFICE
CERTIFICATE OF CORRECTION

PATENT NO. : 4,596,795
DATED : June 24, 1986
INVENTOR(S) : PITHA, Josef

It is certified that error appears in the above-indentified patent and that said Letters Patent is hereby corrected as shown below:

Rewrite claim 1 as 1. (corrected): A method of treating a human by sex hormone addition which comprises [injecting] <u>administering</u> by the buccal route a regimen of 0.1 - 25 mg. per diem of a compound <u>selected from the group</u> consisting of testosterone, progesterone, and estradiol as an inclusion complex with poly-/β-cyclodextrin or hydroxypropyl-/β- cyclodextrin.

Signed and Sealed this

Twenty-ninth Day of July, 1997

Attest:

BRUCE LEHMAN

Attesting Officer        Commissioner of Patents and Trademarks